United States Patent
Morck et al.

(10) Patent No.: US 6,793,900 B1
(45) Date of Patent: Sep. 21, 2004

(54) METHOD AND APPARATUS FOR REDUCING OUTBREAKS OF DIFFUSE LAMELLAR KERATITIS

(75) Inventors: Douglas W. Morck, #4306 - 800 Towerlane Drive, Airdrie, Alberta (CA), T4B 2L1; Simon P. Holland, 3570 W. 19th Avenue, Vancouver, British Columbia (CA), V6S 1C4

(73) Assignees: Douglas W. Morck, Airdrie (CA); Simon P. Holland, Vancouver (CA)

( * ) Notice: Subject to any disclaimer, the term of this patent is extended or adjusted under 35 U.S.C. 154(b) by 0 days.

(21) Appl. No.: 09/538,821

(22) Filed: Mar. 30, 2000

(30) Foreign Application Priority Data

Oct. 22, 1999 (CA) .............................................. 2287150

(51) Int. Cl.[7] .................................................. A61L 2/07
(52) U.S. Cl. ........................................ 422/298; 422/26
(58) Field of Search ........................... 422/26, 299, 113, 422/292, 298

(56) References Cited

U.S. PATENT DOCUMENTS

| | | | | |
|---|---|---|---|---|
| 3,717,434 A | * | 2/1973 | Black .......................... | 422/112 |
| 3,734,154 A | * | 5/1973 | Polk .............................. | 383/57 |
| 4,263,258 A | * | 4/1981 | Kalasek ....................... | 422/113 |
| 4,548,344 A | * | 10/1985 | Hestehave et al. ........ | 222/464.3 |
| 4,851,642 A | * | 7/1989 | Wilkins ....................... | 392/399 |
| 5,271,893 A | * | 12/1993 | Newman ....................... | 422/26 |
| 5,424,047 A | * | 6/1995 | Zwingenberger et al. ... | 422/296 |
| 5,543,119 A | * | 8/1996 | Sutter et al. ................ | 422/299 |
| 5,671,868 A | * | 9/1997 | Herr .............................. | 222/1 |
| 5,972,196 A | * | 10/1999 | Murphy et al. ............. | 205/466 |

FOREIGN PATENT DOCUMENTS

DE      3103381 A   * 11/1982

* cited by examiner

*Primary Examiner*—Elizabeth McKane
(74) *Attorney, Agent, or Firm*—Greer, Burns & Crain, Ltd.

(57) ABSTRACT

Diffuse lamellar keratitis or DLK is a recently recognised post-surgical condition involving an inflammation that occurs in laser corneal surgery patients. This condition is typically associated with the LASIK surgical procedure (Laser Assisted In Situ Keratomileusis). The cause is presently unknown. the present invention provides a sterilization apparatus, which may be a retrofitting of the existing sterilizer, which reduces the occurrence of DLK and also methods for maintaining the sterilizer to reduce the occurrence of DLK.

15 Claims, 4 Drawing Sheets

METHOD AND APPARATUS FOR REDUCING OUTBREAKS OF DIFFUSE LAMELLAR KERATITIS

TECHNICAL FIELD

The invention relates to methods and apparatus for sterilization of ophthalmo-logical instruments, and more particularly to sterilization methods and apparatus for reducing outbreaks of diffuse lamellar keratitis.

BACKGROUND ART

Diffuse lamellar keratitis or DlX (also referred to as "Sands of the Sahara keratitis") is a recently recognised post-surgical condition involving an inflammation that occurs in laser corneal surgery patients. This condition is typically associated with the LASIK surgical procedure (Laser Assisted In Situ Keratomileusis), the most rapidly increasing laser corneal surgery procedure in North America. It usually occurs in the first few days postoperatively. In LASIK surgery, surgeons cut a flap of the cornea and fold it back to expose the layer below, which is shaped with the laser to correct the patient's vision. The corneal flap is then put back in place. The DLK condition, an inflammatory. infection, can develop under the corneal flap and can threaten the patient's sight. DLK usually responds to intensive topical steroids, with lifting of the flap and irrigation in more advanced stages. Untreated or severe cases may progress to melting of the flap with the potential for significant loss of vision. It can occur at low levels in some surgical clinics, however, massive outbreaks have also occurred, where 30–80% of patients receiving the surgical procedure at a clinic may be affected. To date the cause of the complication is not known. Some authors have suggested deposits from the microkeratome blade as a cause of DLK. Others relate DLK to particles from the eye drape. Since the use of laser surgery to correct vision is a relatively new technique which is seeking to be generally accepted, it is important that outbreaks of this inflammation be prevented or at least minimnized.

DISCLOSURE OF INVENTION

The present inventors have discovered a method and apparatus to reduce outbreaks of the DLK inflammation. Instrument sterilizers are used to prepare surgical materials for the LASIK procedure. These sterilizers have a holding tank, or reservoir, that supplies water to be turned into steam for the sterilization. If these holding tanks become contaminated with specific biofilm bacteria they can become a source of certain toxins (lipopolysaccharide or endotoxin) that can be released into the sterilizer system and deposited on the surgical instruments that are to be used in the delicate structures of the eye (corneal stroma). These toxins are extremely heat stable (400° F. for 4 hours is required to destroy them) therefore they are not destroyed by the short sterilization cycles provided by the sterilizers in these surgical clinics. As a result of this it is imperative to remove these biofilm bacteria from the reservoirs and to keep the reservoirs free of subsequent contamination by biofilm bacteria.

The present invention therefore provides a method to remove biofilm bacteria from the reservoirs in these sterilizers, a method to prevent biofilm bacteria from contaminating the reservoirs, and an external reservoir that may be fitted on existing sterilizers, by-passing the existing internal reservoirs, that is simple to use and on which it is very easy to conduct preventative anti-bioflim procedures.

BRIEF DESCRIPTION OF DRAWINGS

In drawings which illustrate a preferred embodiment of the invention.

BEST MODE(S) FOR CARRYING OUT THE INVENTION

Figure 1:
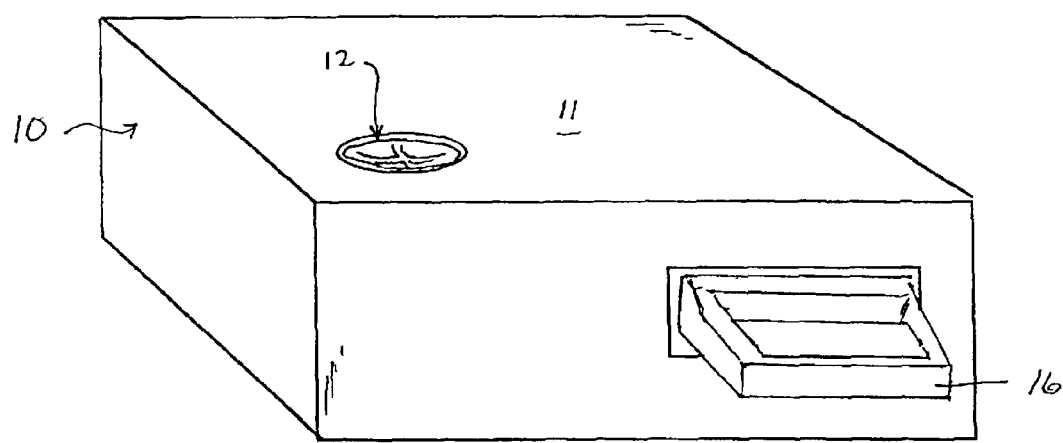
FIG. 1 is a front perspective view of the existing sterilization equipment.

Currently in laser eye surgery, instrument sterilizers are used to sterilize the surgical instruments for the LASIK procedure between each patient. Since a rapid rate of sterilization is required due to high patient turnover, the preferred sterilizers have been autoclaves used previously in dental practices, as illustrated in FIG. 1, designated generally by reference numeral 10. For example, the preferred and widely used sterilizer is the STATIM™ cassette autoclave manufactured by SciCan Division of Lux and Zwingenberger Ltd., and in particular the STATIM 5000™. Such a sterilizer is described in U.S. Pat. No. 5,271,893—Newman issued Dec. 21, 1993. Another commonly used sterilizer is the AMSCO Eagle 10™ manufactured by Steris of Mentor, Ohio. These sterilizers have a 4 to 10 minute sterilization cycle and use steam injection to achieve sterilization. They typically have an internal holding tank, or reservoir 12 within housing 11, lined with plastic and having an irregular surface, which holds and supplies distilled water to be heated for the sterilization. The distilled water flows, by pump or gravity feed, through rubber tubing to a dosing pump 13 and a steam generator or boiler unit 14, which provides steam under pressure to the cassette 16 in which the surgical instruments to be sterilized are placed. In more recent models, an air pump (not shown) pumps the distilled water through an external, replaceable filter 19, prior to its injection into the boiler unit 14.

The present inventors believe that endotoxins released from gram negative bacterial biofilms in sterilizer reservoirs may be the cause of outbreaks of DLK. The irregular plastic surfaces of the reservoirs are ideal for bacterial biofilm development and if the holding tanks 12 become contaminated with specific biofilm bacteria they can become a source of certain toxins (lipopolysaccharide or endotoxin) that can be released into the sterilizer system and deposited on the surgical instruments that are to be used in the delicate structures of the eye (corneal stroma). These toxins are extremely heat stable (can withstand up to 400° F. for 4 hours) therefore they are not destroyed by the short sterilization cycles provided by the sterilizers in these surgical clinics. As a result of this it is imperative to remove these biofilm bacteria from the reservoirs and to keep the reservoirs free of subsequent contamination by biofilm bacteria. The present invention therefore is a methodology to remove biofilm bacteria from the reservoirs in these sterilizers and to prevent biofilm bacteria from contaminating the reservoirs. Further, the inventors have also developed a special external reservoir that may be retrofitted to existing sterilizers, by-passing the existing internal reservoirs, that is simple to use and on which it is very easy to conduct preventative anti-biofilm procedures.

Investigations of certain outbreaks of DLK show similar features in support of the endotoxin-outbreak DLK theory. In a first case *Burkholderia pickettii* was isolated from the sterilizer reservoir; in a second case *Burkholderia* (*Pseudomonas*) *cepacia* was isolated from the STATIM™ sterilizer reservoirs and from a tabletop distiller. The outbreak was brought under control by using similar methods to those described herein, w to disinfect the sterilizer reservoir. All cases were related to sterilizer reservoir contamination with a Burkholdetia or Pseudomonas species. After implementing the control measures described herein the attack rate of DLK was significantly reduced.

A. Sterilizer Modification

A separate, removable re-usable reservoir 20 (FIG. 2 and 3) is provided for storing sterile, endotoxin free distilled water. Preferably it is manufactured from a substance which can be subjected to sufficiently high temperatures to destroy endotoxins, preferably Pyrex™ glass or stainless steel. It has a threaded neck 22, and a polished lip 24, to receive a threaded stainless steel cap 26 sealed with 0-ring 28 and provided with a nipple 30 to which biotechnology grade silicon tubing 32 is connected to feed distilled water directly to the heating unit 14 of sterilizer 10. Tubing 32 may be either disposable or re-usable. The reservoir 20 is provided with an air release valve 34 which is opened when the reservoir is inverted and the system operating to provide air pressure for the gravity feed. The reservoir 20 is preferably wall-mounted on a mounting bracket 21 and easily removable so that its inside surfaces can be scrubbed and subjected to long periods of high temperature.

According to an alternate embodiment, a disposable external reservoir may be used in place of reservoir 20. This may be a commercially available bag or bottle of sterile endotoxin-free (non-pyrogenic) distilled water used for irrigation similar to those used for bags or bottles for intravenous fluids for patient use. Suitable disposable bags/bottles of sterile endotoxin-free (non-pyrogenic) distilled water are available from Baxter Corp., Abbott Laboratories, and others. The disposable external reservoir may be directly attached to the water supply line of existing models of sterilizer units such as the STATIM™, as described above for the re-usable reservoir 20, but when empty the disposable reservoir is simply disposed and replaced.

Figure 4:
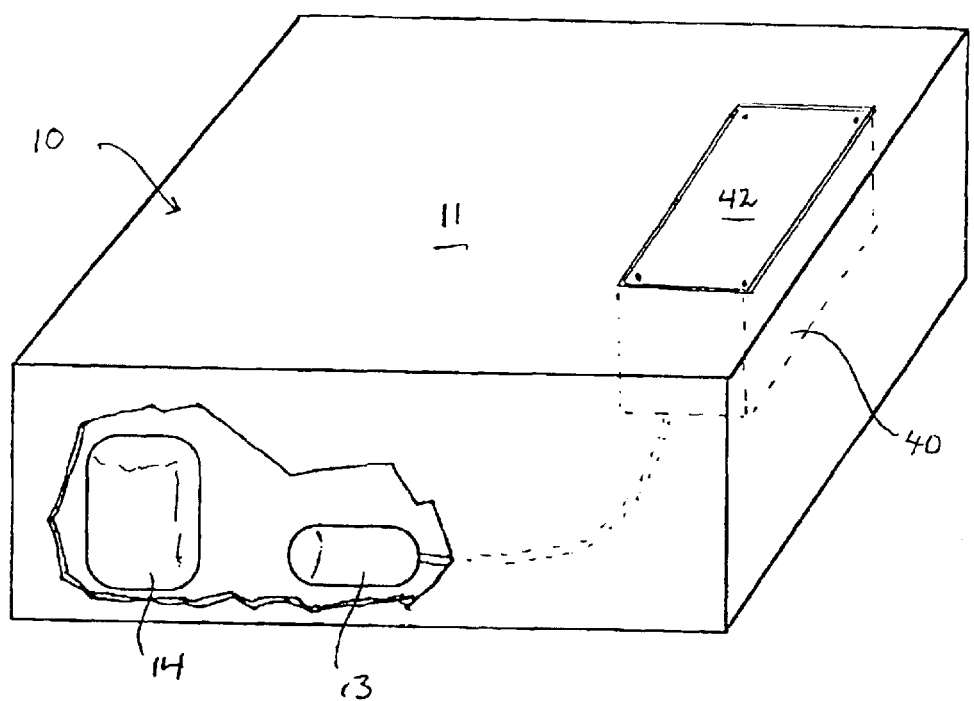
FIG. 4 is a rear perspective view of a further embodiment of the invention.

According to yet another alternate embodiment, a disposable, removable internal reservoir 40 (shown in dotted outline in FIG. 4) may be used in place of reservoir 12 inside the housing 11 of sterilizer 10. This may be a container made of, or lined with high density polyethylene (HDPE) or similar plastic. The disposable removable reservoir is previously filled with sterile endotoxin-free (non-pyrogenic) distilled water, or it can be filled after insertion into the housing 11 through a closable opening 42 in the container. The reservoir is inserted into an appropriately sized cavity in sterilizer housing 11 through a closable opening 42 in housing 11 and directly attached to the water supply line for the sterilizer 13/14 by means of disposable SILASTIC™ tubing. The removable reservoir 40 and attached tubing is removed, disposed of and replaced periodically, depending on the amount of use, to avoid build-up of biofilm and endotoxins. Typically this will be on a weekly basis.

Figure 2:
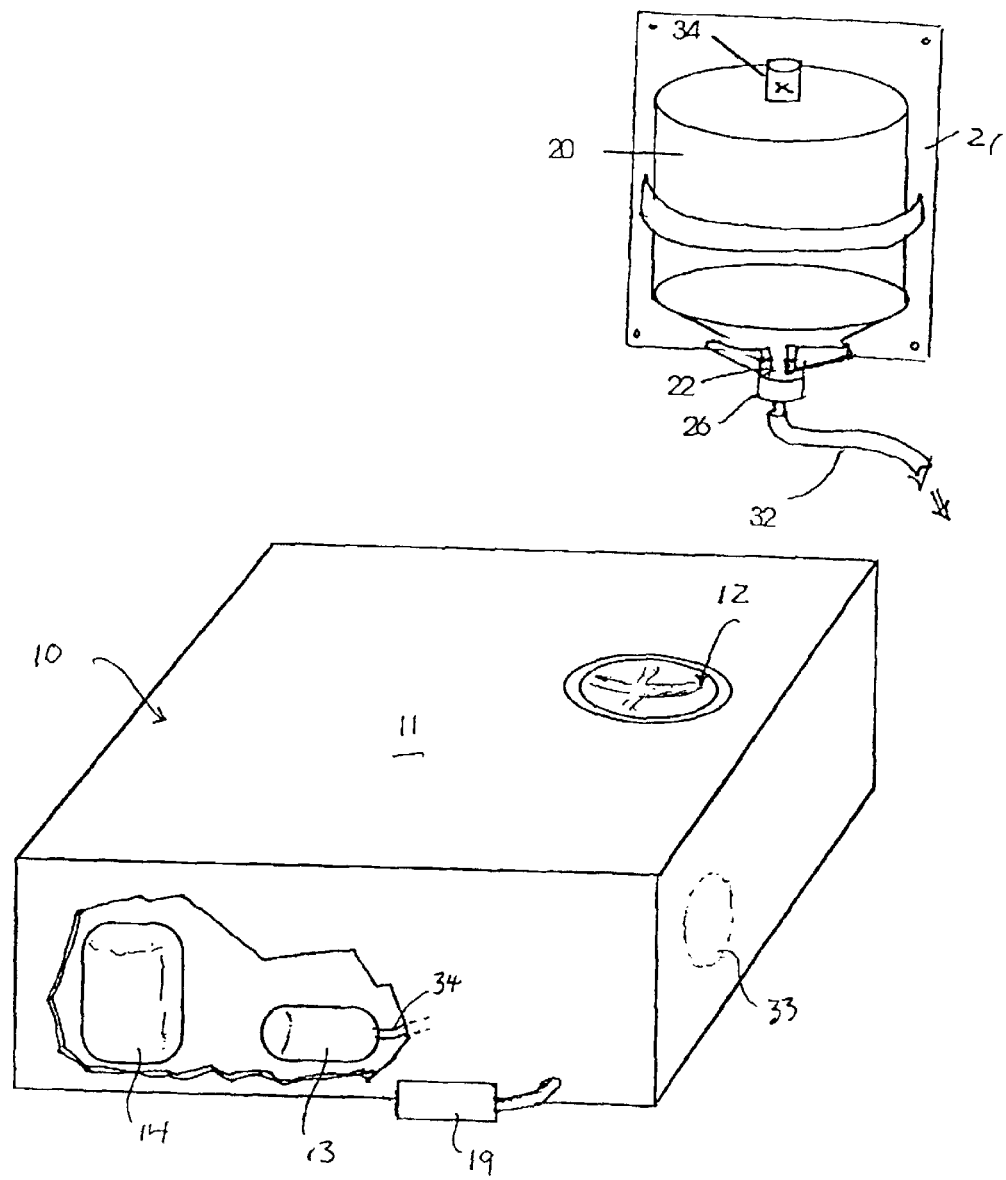
FIG. 2 is a rear perspective view of the existing sterilization equipment modified according to the invention.
Figure 3:
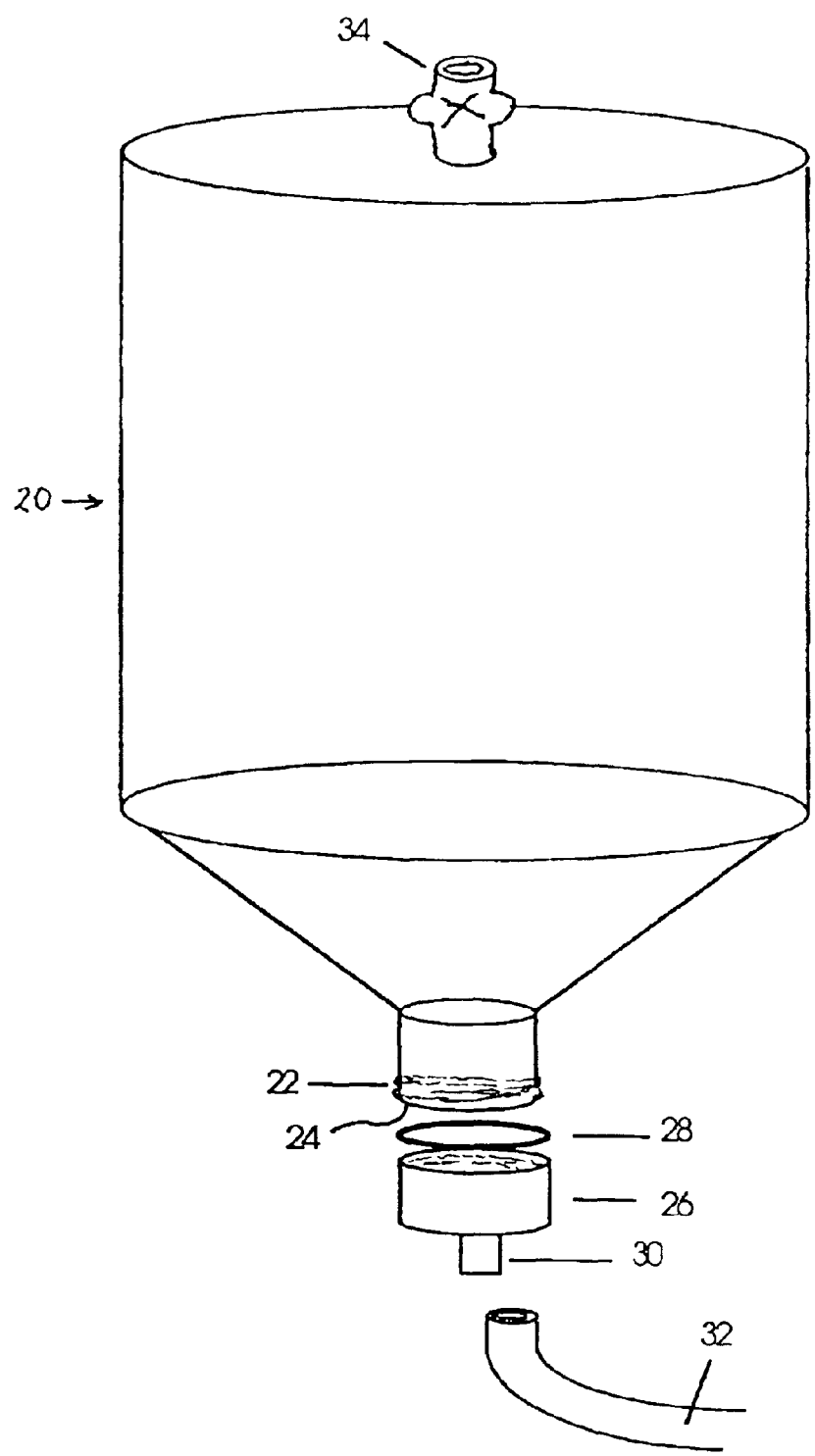
FIG. 3 is a front view of the water reservoir used in the sterilization equipment modified according to the invention.

The foregoing removable reservoir 20, whether reusable or disposable, can be manufactured as part of a new sterilizer of the STATIM™ type. or retrofitted to existing sterilizers. Where the sterilizer has an external filter 19, as shown in FIG. 2, or where there is no external filter 19, the output tubing 32 from the reservoir 20 is connected to the line 34 leading from holding tank 12 to the boiler unit 14. It may be necessary to cut a hole 33 in the sterilizer casing to allow access of output tubing 32 to the input to the boiler unit 14. Alternatively, the sterilizer may be manufactured without the internal reservoir 12 but rather with a built-in tubing connection to the external removable reservoir 20.

Where it is not desirable or possible to provide a removable reservoir as noted above, the following methods have been found to control DLK outbreaks. These involve first a system of draining the sterilizer at the end of each surgical day and using mechanical scrubbing and boiling water treatments in the morning prior to and at the end of each surgical day. At longer intervals, an isopropyl alcohol solution at about 70% was also placed in the sterilizer at the end of the surgical day, allowed to evaporate and then the boiling water treatment performed. These methods are considered unlikely to damage the polymer lining.

B. Sterilizer Maintenance Procedure

This method is carried out on a daily basis as follows:

i) Start of the Surgery Day

1. Fill the empty reservoir with boiling tap water and drain using the sterilizer's pump.
2. Fill the reservoir with boiling tap water and drain using the pump.
3. Rinse the reservoir by filling with room temperature distilled water and drain with the pump.
4. Rinse the reservoir by filling with room temperature distilled water and drain with the pump.
5. Rinse the reservoir by filling with room temperature distilled water and drain with the pump.
6. Prepare and conduct the first sterilization run of instruments.

ii) End of the Surgery Day

1. Drain the sterilizer reservoir with the pump.
2. Fill the reservoir with boiling water and scrub the entire inner surface of the reservoir with a clean brush.
3. Drain the reservoir with the pump.
4. Fill the reservoir with boiling water and scrub the entire inner surface of the reservoir, again with a clean brush.
5. Drain the reservoir with the pump.
6. Rinse the reservoir by filling and draining the reservoir three (3) times with room temperature distilled water.
7. Fill the reservoir with isopropyl alcohol (70%) and scrub the inner surface of the reservoir with the rinsed clean brush.
8. Drain the reservoir with the pump.
9. Rinse the reservoir by filling and draining the reservoir three (3) times with room temperature distilled water.
10. Dry the inside of the reservoir with hair dryer or wipe the inside of the reservoir dry with a clean cloth.
11. Store the reservoir empty and dry overnight.
12. Change the rubber tube inside the reservoir weekly.

C. Major Sterilizer Clean up Procedure

This method is carried out on a less frequent basis, perhaps a quarterly basis (every 13 to 14 weeks).

1. Fill the empty reservoir with boiling tap water, add disinfectant (hypochlorite), and vigorously scrub using the clean brush (15 minutes and the scrub must cover all of the inner surface of the reservoir). Drain using the pump.
2. Fill the empty reservoir with boiling tap water, add disinfectant, and vigorously scrub using the clean brush (15 minutes and the scrub must cover all of the inner surface of the reservoir). Drain using the pump.
3. Fill the empty reservoir with boiling tap water, add disinfectant, and vigorously scrub using the clean brush (15 minutes and the scrub must cover all of the inner surface of the reservoir). Drain using the pump.

4. Pill the empty reservoir with boiling tap water, add disinfectant, and vigorously scrub using the clean brush (15 minutes and the scrub must cover all of the inner surface of the reservoir). Drain using the pump.
5. Fill the reservoir with boiling tap water and drain using the pump.
6. Fill the reservoir with boiling tap water and drain using the pump.
7. Fill the reservoir with boiling tap water and drain using the pump.
8. Rinse the reservoir by filling with room temperature distilled water and drain with the pump.
9. Rinse the reservoir by filling with room temperature distilled water and drain with the pump.
10. Rinse the reservoir by filling with room temperature distilled water and drain with the pump.
11. Fill the reservoir with isopropyl alcohol (70%) and scrub the inner surface of the reservoir with the very well rinsed clean brush.
12. Drain the reservoir with the pump.
13. Rinse the reservoir by filling and draining the reservoir three (3) times with room temperature distilled water.
14. Dry the inside of the reservoir with hair dryer or wipe the inside of the reservoir dry with a clean cloth.
15. Store the reservoir empty and dry overnight.
16. Change the rubber tube inside the reservoir weekly.

While the foregoing apparatus and methods have been found useful to reduce outbreaks of diffuse lamellar keratitis, they are also believed to be useful for reducing outbreaks of other aseptic inflammations of the eye resulting from eye surgery, such as sterile endophthalmitis.

While isopropyl alcohol (70%) has been identified as an appropriate agent in the forgoing process, other solvents such as ethanol, methanol and acetone would also be suitable.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. An apparatus for reducing outbreaks of aseptic inflammations of the eye resulting from eye surgery comprising a sterilizer for sterilizing medical instruments used in said eye surgery with steam comprising a housing containing a steam generator supplied by a dispensing pump and a sterilization container for containing said medical instruments supplied with steam by said steam generator, and further comprising a reservoir of for containing distilled water which holds and supplies distilled water to said steam generator, and means for liquid communication between said reservoir and said dispensing pump and between said dispensing pump and said steam generator, wherein said reservoir is separable and removable from said housing for purpose of destroying endotoxins in said reservoir by heat and is manufactured from a substance which is capable of withstanding without damage a temperature which is sufficiently high for a sufficient period of time to destroy endotoxins.

2. The apparatus of claim 1 wherein said reservoir is separate and free standing apart from said housing.

3. The apparatus of claim 1 wherein said reservoir is manufactured from Pyrex glass.

4. The apparatus of claim 1 wherein said reservoir is manufactured from stainless steel.

5. The apparatus of claim 1 wherein said reservoir comprises a hollow vessel having a threaded neck to sealingly receive a threaded cap provided with means to receive a tubing for connecting said reservoir to said steam generating unit.

6. The apparatus of claim 1 wherein said reservoir is adapted to be inverted in use and is provided with an air release valve which is opened when the reservoir is inverted and the system operating.

7. The apparatus of claim 1 wherein said temperature is greater than 400 degrees Fahrenheit and said period of time is at least 4 hours.

8. The apparatus of claim 1 wherein said reservoir is mounted externally of said housing.

9. The apparatus of claim 1 wherein said reservoir is retrofitted to an apparatus already having a non-removable reservoir within said housing.

10. An apparatus for reducing outbreaks of aseptic inflammations of the eye resulting from eye surgery comprising a sterilizer for sterilizing medical instruments used in said eye surgery with steam comprising a housing containing a steam generator supplied by a dispensing pump and a sterilization container for containing said medical instruments, and further comprising a reservoir for containing distilled water which holds and supplies distilled water to said steam generator, and means for liquid communication between said reservoir and said dispensing pump and between said dispensing pump and said steam generator, wherein said reservoir is a replaceable reservoir of sterile endotoxin-free distilled water adapted to be removed and replaced when emptied of distilled water.

11. The apparatus of claim 10 wherein said replaceable reservoir is mounted eternally of said housing.

12. The apparatus of claim 11 wherein said replaceable reservoir is retrofitted to an apparatus ready having a non-removable reservoir within said housing.

13. The apparatus of claim 10 wherein said reservoir is a disposable, removable reservoir adapted to be removably contained within said housing.

14. The apparatus of claim 13 wherein said removable reservoir is a bag of sterile endotoxin-free distilled water.

15. The apparatus of claim 13 wherein said removable reservoir is a bottle of sterile endotoxin-free distilled water.

* * * * *

UNITED STATES PATENT AND TRADEMARK OFFICE
CERTIFICATE OF CORRECTION

PATENT NO. : 6,793,900 B1
DATED : September 21, 2004
INVENTOR(S) : Morck et al.

It is certified that error appears in the above-identified patent and that said Letters Patent is hereby corrected as shown below:

Column 1,
Line 8, after "ophthalmo" and before "logical", delete "-";
Line 13, change "DIX" to -- DLK --;
Line 25, after "matory" delete "." .

Column 3,
Line 8, after "herein," delete "w";
Line 10, change "Burkholdetia" to -- Burkholderia --;
Line 20, change "0" to -- O --.

Column 5,
Line 1, change "Pill" to -- Fill --;
Line 50, delete "of".

Column 6,
Line 43, change "eternally" to -- externally --;
Line 45, change "ready" to -- already --.

Signed and Sealed this

Twenty-sixth Day of April, 2005

JON W. DUDAS
*Director of the United States Patent and Trademark Office*